US00PP33318P2

(12) United States Plant Patent
Hansen

(10) Patent No.: US PP33,318 P2
(45) Date of Patent: Aug. 3, 2021

(54) ***HOSTA* PLANT NAMED 'DROP-DEAD GORGEOUS'**

(50) Latin Name: ***Hosta* hybrid (Tratt.)**
Varietal Denomination: Drop-dead Gorgeous

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,101

(22) Filed: Sep. 30, 2020

(51) Int. Cl.
*A01H 5/12* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 6/12
See application file for complete search history.

(56) References Cited

PUBLICATIONS

The *Hosta* Helper, *Hosta* 'Drop-dead Gorgeous' from PlantsGalore, http://www.plantsgalore.com/hostas/cultivars/D/Hosta_Drop-dead_Gorgeous.htm, downloaded Jan. 19, 2021.*

* cited by examiner

*Primary Examiner* — Anne Marie Grunberg

(57) ABSTRACT

A new and distinct *Hosta* plant named 'Drop-dead Gorgeous' of very large, arching, long, ovate, green leaves having wavy yellow margins. The flowers are white with light lavender veins and blushing. Prior to flower bud opening, the floral bracts produce a broad, short, light lavender, water-lily effect of compact lanceolate bracts. 'Drop-dead Gorgeous' has excellent very large mounded habit and is useful in the landscape, as a specimen or en masse.

2 Drawing Sheets

Botanical classification: *Hosta* hybrid (Tratt.).
Variety denomination: 'Drop-dead Gorgeous'.

STATEMENT REGARDING PRIOR DISCLOSURES UNDER 37 CFR 1.77(b)(6)

*Hosta* 'Drop-dead Gorgeous' was first introduced by the inventor as a non-enabling description through the International Cultivar Registration Authority registration in early 2020. No plants of *Hosta* 'Drop-dead Gorgeous' have been sold, in this country or anywhere in the world, nor has any disclosure of the new plant been made, more than one year prior the filing date of this application.

BACKGROUND AND ORIGIN OF THE PLANT

The present invention relates to a new and distinct *Hosta* plant, *Hosta* 'Drop-dead Gorgeous' hereinafter also referred to as the new plant or by the cultivar name, 'Drop-dead Gorgeous'. *Hosta* 'Drop-dead Gorgeous' was a cross by the inventor between two non-patented, unreleased, proprietary hybrids on Jun. 14, 2012 at a wholesale perennial nursery in Zeeland, Mich., USA. The female parent was identified as a proprietary, unreleased sport known only as "streaked 'Niagara Falls'" (not patented) and the male parent was 'Empress Wu' U.S. Plant Pat. No. 20,774. The new plant was assigned the breeder code 12-115-4 and passed the initial evaluation in the summer of 2014. It has been asexually propagated by division at the same nursery since 2018 and also by careful shoot tip plant tissue culture with the resultant asexually propagated plants having retained all the same traits as the original plant. *Hosta* 'Drop-dead Gorgeous' is stable and reproduces true to type in successive generations of asexual reproduction.

There are nearly 7,000 registered and established *Hosta* cultivars with The American *Hosta* Society, which is the International Cultivar Registration Authority for the genus *Hosta*. Several of these have green leaf blades with variegated margins. The most similar *Hosta* cultivars known to the applicant are 'Bridal Falls' U.S. Plant Pat. No. 25,594, 'Atlantis' U.S. Plant Pat. No. 17,093, 'Satisfaction' (not patented) and 'Wu-La-La' U.S. Plant Pat. No. 31,309.

'Bridal Falls' has similar ruffled margins, but the variegation is creamy-white. 'Atlantis' has a more pointed leaf blade and the margin is not as ruffled. 'Satisfaction' has leaves that are more bullate and the margin is less ruffled. 'Wu-La-La' has a larger habit and a more rounded leaf with a thinner variegated margin that is not ruffled. The female parent has leaves with random streaked variegation in the margin and center with ruffled leaf margins. The male parent has larger leaves and much larger habit with slightly glaucous leaves that are not variegated.

Other *Hosta* cultivars may have ovate leaf blades with yellow variegated margins and green centers, thick leaf substance or other individual traits similar to 'Drop-dead Gorgeous' but the new plant differs from the above listed cultivars and all other *Hostas* known to the applicant, by the combination of the following traits.

1. Leaves are very large-sized, long, ovate, with broadly acute apices and cordate base;
2. Arching leaves have a moderately-wavy yellow margin;

3. Leaf center is dark green with numerous featherings of intermediate colors between the margin and center;
4. Flowers are white, faintly blushed with light lavender and densely arranged on scapes with the first flowers beginning to open above the foliage;
5. Floral bracts form broad, short, light-lavender, water-lily effect well before flowers buds open;
6. Very large mounded habit and useful in the garden as edging or front border, in containers, as a specimen or en masse.

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source and direction may cause the appearance of minor variation in color.

The drawings show a seven-year-old 'Drop-dead Gorgeous' plant in a trial garden at a nursery in Zeeland, Mich. with supplement fertilizer and water as needed.

DETAILED BOTANICAL DESCRIPTION

Figure 1:
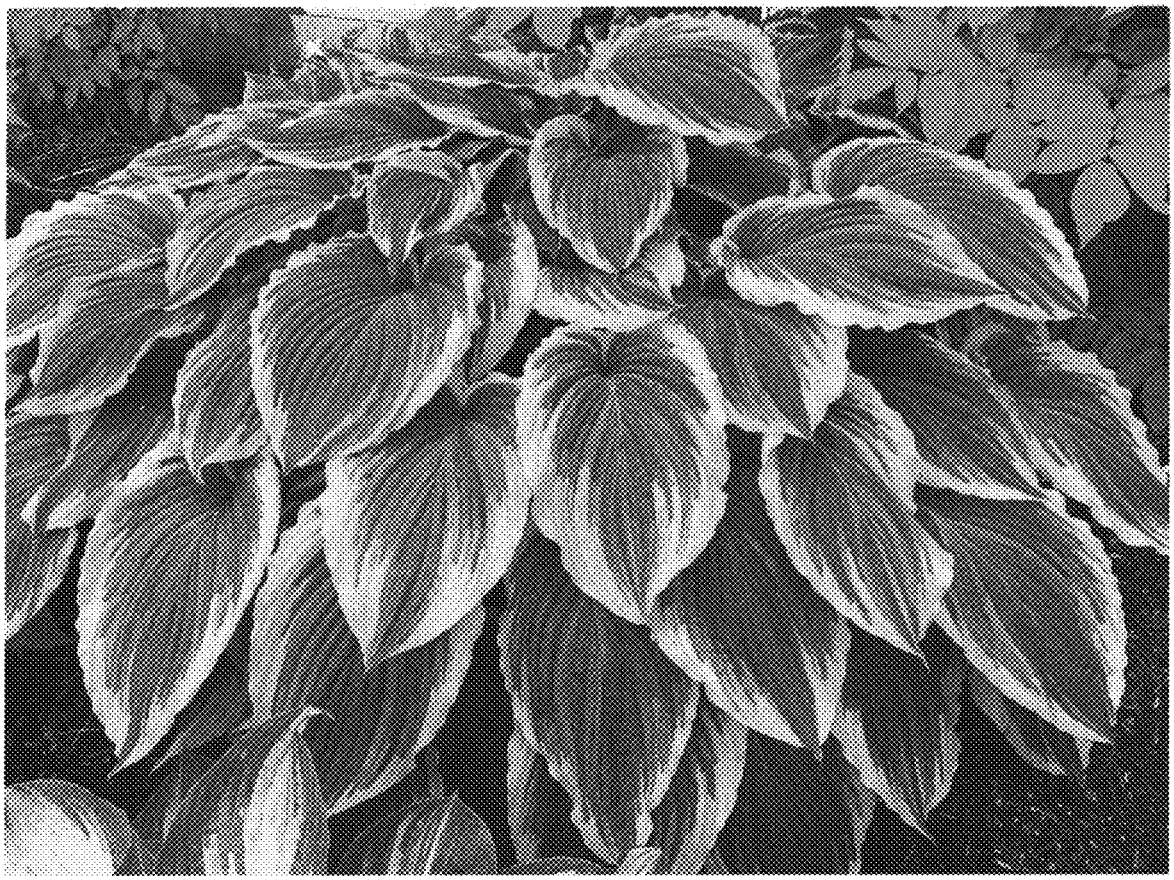
FIG. 1 shows the landscape foliage habit of a new plant just before flowering.
Figure 2:
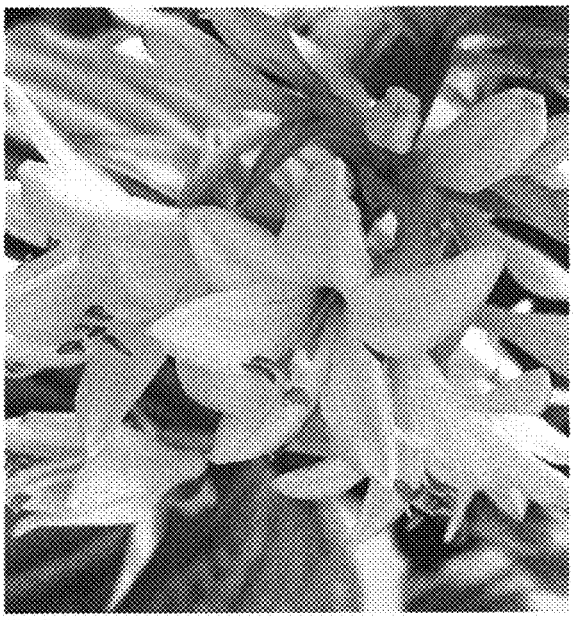
FIG. 2 shows a close-up of the flowers and buds.
Figure 3:
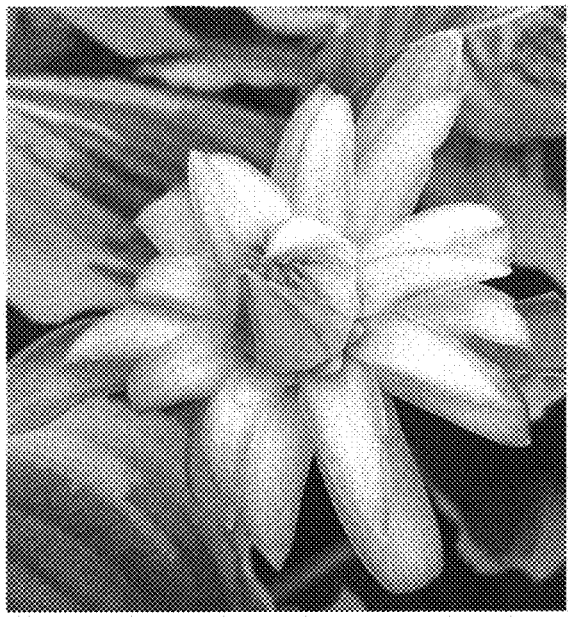
FIG. 3 shows a close-up of the immature flower scape with colorful bracts.
Figure 4:
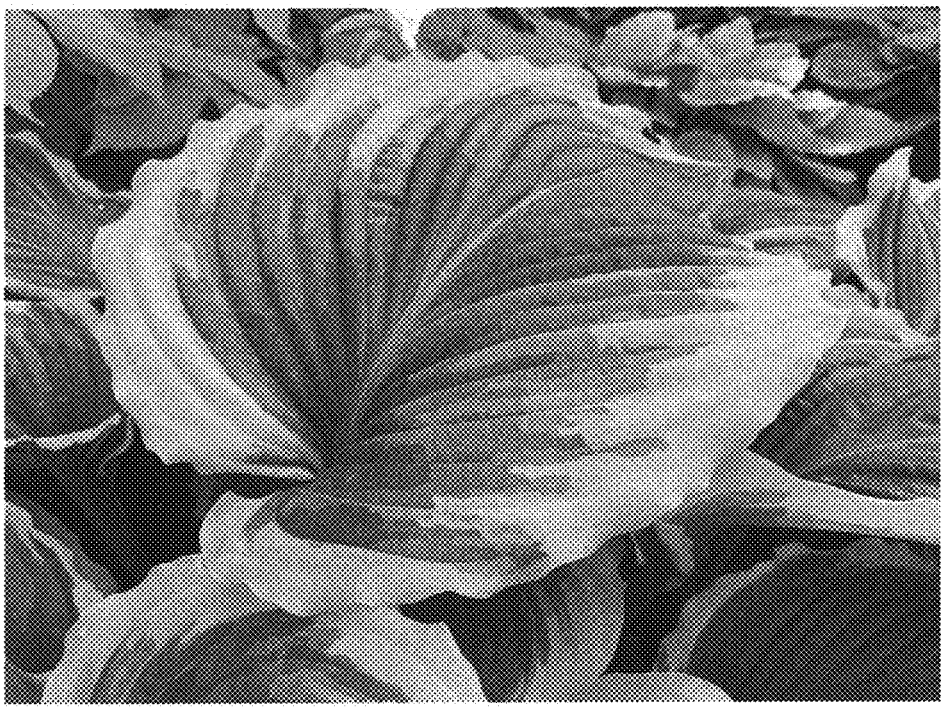
FIG. 4 shows a close-up of the foliage.

The following descriptions and color references are based on the 2015 edition of The Royal Horticultural Society Colour Chart except where common dictionary terms are used. The new plant, *Hosta* 'Drop-dead Gorgeous', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a seven-year-old plant in a shaded trial garden in Zeeland, Mich. with supplemental water and fertilizer.

Botanical classification: *Hosta* x hybrid;

Parentage: Female or seed parent the proprietary "'Niagara Falls' streaked"; male or pollen parent 'Empress Wu';

Propagation: Garden division and sterile shoot tip plant tissue culture;

Time to initiate roots from tissue culture: About two to three weeks;

Growth rate: Moderately vigorous;

Crop time: About three months to four months to finish during the spring in a one-liter container from rooted tissue culture plantlet;

Rooting habit: Fleshy, lightly branching;

Root color: Nearest RHS NN155C when actively growing;

Plant shape and habit: Hardy herbaceous perennial with basal rosette of leaves emerging from rhizomes producing a large mound of arching petioles and leaves and erect scapes flowering above foliage;

Plant size: Foliage height to about 76.2 cm above soil line to the top of the leaves, to about 104.1 cm tall to the top of the flowers and to about 218.4.0 cm wide at the widest point at the soil line;

Foliage description: Ovate; narrowly acute apex, cordate base; margin entire, heavily sinuate; glabrous both surfaces, and. adaxial matte and abaxial lustrous when young becoming slightly glaucous with maturity; flexible but stiff; smooth, without blistering, dimpling or bulging; deeply impressed adaxial veins and costate abaxial veins; leaf blade profile tends to be slightly cupped only on inner shoot leaves early in the season, and all leaves tend to become flat to slightly arched distally later in season;

Leaf blade size: To about 43.2 cm long and about 28.0 cm wide about one-half of the way from the base; average about 36.5 cm long and 24.7 cm wide; margin width to about 2.5 cm wide, average 2.0 cm wide;

Leaf blade color: Early season and expanding adaxial margin nearest RHS 145C and abaxial margin nearest blend between HRS 145C and RHS 145D, adaxial center nearest RHS 146C and abaxial center between RHS 146B and RHS 146C, adaxial intermediate colors comprising RHS 148D and RHS 146D, abaxial intermediate colors comprising RHA 147D and between RHS 148D and RHS 146D; mid-season and mature adaxial margins between RHS 11B and THS 160D, abaxial margin between RHS 150D and RHS 160D, adaxial center between RHS 137A and RHS NN137D, abaxial center between RHS 189A and RHS NN137D, adaxial intermediate colors comprising RHS 188C, RHS N138D and RHS145A with RHS N138D undertones, abaxial intermediate colors comprising RHS 145B, RHS 145D and RHS 144B;

Petiole: Glabrous and slightly glaucous both adaxial and abaxial; deeply concavo-convex proximally and more shallowly concavo-convex distally; stiff; to 64.5 cm long and 16.0 mm wide at base and about 10.0 mm deep near base, average about 58.0 cm long and 14.0 mm wide;

Petiole color: Adaxial center between RHS 145A and RHS 146D, margins about 1.0 mm wide nearest RHS 150D; abaxial center between RHS 145A and RHS 146D, margins about 1.0 mm wide nearest RHS 150D;

Veins: Thirteen to fourteen pairs and midrib; parallel; deeply impressed adaxial; costate and asperous abaxial;

Veins color: Adaxial nearest RHS 150D; abaxial nearest RHS 148D;

Flower description:

Buds one to two days prior to opening: Clavate with rounded apex and narrow tube base; about 37.0 mm long and 8.0 mm in diameter at widest with base narrowing in basal 12.0 mm to about 3.0 mm diameter;

Bud color: Nearest RHS NN155D distally and nearest RHS 155C proximally;

Flowers: Perfect; flared campanulate; outwardly; to 37.0 mm long to exserted stigma; corolla fused in basal 20.0 mm, free in the distal 17.0 mm, about 37.0 mm long and 30.0 mm wide at tepal apices, decreasing distally; corolla tube portion 12.0 mm long and 3.0 mm diameter; persists for a normal period, usually about one day on plant; flowers tightly arranged on scape;

Flowering period: Scapes remain effective with flowers beginning early-July for about four and a half weeks; with about 60 flowers per scape; mostly secund;

Fragrance: No detectable fragrance;

Tepal: Two nearly identical sets of three, glabrous; entire margins;

*Inner set.*—About 39.0 mm long and 8.0 mm wide slightly above fusion point; fused in basal 20.0 mm;

clavate with broadly acute apex; entire margin with 1.0 mm wide transparent border; base fused into tube.

*Inner set color.*—Vitreous along margin; adaxial and abaxial nearest RHS NN155D with adaxial having very faintly blushed distal veins less pink and more lavender than RHS 76D; corolla tube base adaxial and abaxial between RHS 76B and RHS 76C.

*Outer set.*—About 39.0 mm long and 8.0 mm wide slightly above fusion point; fused in basal 20.0 mm; clavate with broadly acute apex; entire margin without transparent border; base fused into tube.

*Outer set color.*—Adaxial and abaxial nearest RHS NN155D with adaxial having very faintly blushed distal veins less pink and more lavender than RHS 76D; corolla tube base adaxial and abaxial between RHS 76B and RHS 76C.

Gynoecium: Single; 43.0 mm long; superior;

*Style.*—Cylindrical; about 34.0 mm long, 0.7 mm diameter; curved upward 90 degrees in distal 10.0 mm; color nearest RHS NN155D distally and nearest RHS 145C proximally.

*Stigma.*—Puberulent; tri-lobed; about 1.2 mm across and 1.0 mm tall; color nearest RHS NN155A.

*Ovary.*—Ellipsoidal; superior; apex rounded; base rounded to truncate; to about 6.5 mm long and 2.5 mm diameter in middle; color nearest RHS 145A.

Androecium: Six;

*Filaments.*—Six, approximately 32.0 mm long and 0.3 mm in diameter; curved upward to nearly 90 degrees in the apical 5.0 mm; color distally nearest RHS NN155B, base nearest RHS 145C.

*Anthers.*—Ellipsoidal with rounded ends; near-basifixed, longitudinally dehiscent; about 3.5 mm long and 1.2 mm wide; color prior to dehiscing nearest RHS 164C adaxial and abaxial between RHS 161D and RHS 158A; after dehiscing abaxial nearest RHS 202A.

*Pollen.*—Spherical; less than 0.1 mm long; color nearest RHS 17B.

Flower fragrance: None observed;

Peduncle: Cylindrical; usually one per mature division; about 12 per plant; glabrous, slightly glaucous; erect; to about 104.1 cm tall, and about 10.0 mm in diameter at base, average about 92.0 cm tall and 9.0 mm diameter at base;

Inflorescence: Flowering portion about 30.0 cm long and 8.0 cm wide; with large lavender blushed floral bracts subtending each flower;

Peduncle color: Proximal portion below leaves nearest RHS 138C and distal portion nearest RHS 138A;

Pedicel: Variable in length; terete; glabrous; slightly lustrous; about 10.0 mm to 14.0 mm long and 1.5 mm diameter; outwardly to slightly drooping;

Pedicel color: Variable; distally nearest145D, middle portion nearest RHS 145B, proximally nearest RHS 145A with base nearest RHS NN137D;

Floral bracts: Each flower normally subtended by a single bract; lanceolate; narrowly acute apex and truncate base; entire margin; glabrous and slightly lustrous abaxial and adaxial; to about 8.0 cm long 9.0 mm wide, decreasing distally; prior to flower development forming compact attractive cluster about 12 cm across; drying before flowers open;

Bract color: Young distal adaxial and abaxial nearest RHS 85D near longitudinal center with margins between RHS 85C and RHS 86B, older proximal bracts nearest RHS 145D in longitudinal center with margins between RHS 146D and RHS 145A;

Fruit: Tri-valved dehiscent capsule; ellipsoidal to cylindrical with apex apiculate to acute and attenuate base; about 32.0 mm long and 7.0 mm diameter;

Fruit color: Nearest RHS 146D as maturing and RHS 161D when ripe;

Seed: Typically about 30 per capsule; endospermic; flattened-ellipsoidal wing surrounding embryo at one end of ellipse; to about 9.0 mm long, 3.5 mm wide and 1.5 mm thick at embryo;

Seed color: Nearest RHS 202A;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars. The plant grows best and shows best coloration with plenty of moisture, adequate drainage and light shade, but is able to tolerate some drought when mature. Hardiness at least from USDA zone 3 through 8, and other disease resistance is typical of that of other *Hostas*.

It is claimed:

1. A new and distinct *Hosta* plant cultivar named *Hosta* 'Drop-dead Gorgeous' as herein described and illustrated.

* * * * *